United States Patent [19]

Wandell

[11] Patent Number: Plant 6,709

[45] Date of Patent: Apr. 4, 1989

[54] THORNLESS HONEYLOCUST

[76] Inventor: Willet N. Wandell, Rte. #1, Box 286, Oquawka, Ill. 61469

[21] Appl. No.: 117,337

[22] Filed: Nov. 6, 1987

[51] Int. Cl.[4] ..... A01H 5/00

[52] U.S. Cl. ..... Plt./52

[58] Field of Search ..... Plt. 52

*Primary Examiner*—Robert E. Bagwill

[57] ABSTRACT

A new Thornless Honeylocust being seedless and having a rapid rate of growth and dense crown.

3 Drawing Sheets

This new variety of Thornless Honeylocust was discovered by me growing on cultivated property in Madison, Ohio. The new variety is seedless and thornless and has a distinct broadly pyramidal growth form, a uniform branch angle that conforms into a more dense crown than the species and a more rapid rate of growth than the species demonstrated by the elongation of the first year lateral branches, the second year development of more numerous laterals, the resultant heavy scaffold and the rapid development of caliper in young nursery liners propagated from the parent tree. I have approximately 300 asexually produced trees in my nursery, all of which exhibit the superior qualities of the parent tree.

SUMMARY OF INVENTION

A new and distinct cultivar of Thornless Honeylocust characterized by its distinct broadly pyramidal growth form, high leaf population, the uniform branch angle, heavy dense crown, dark green foliage and rapid rate of growth.

DESCRIPTION OF THE NEW PLANT

Figure 1:
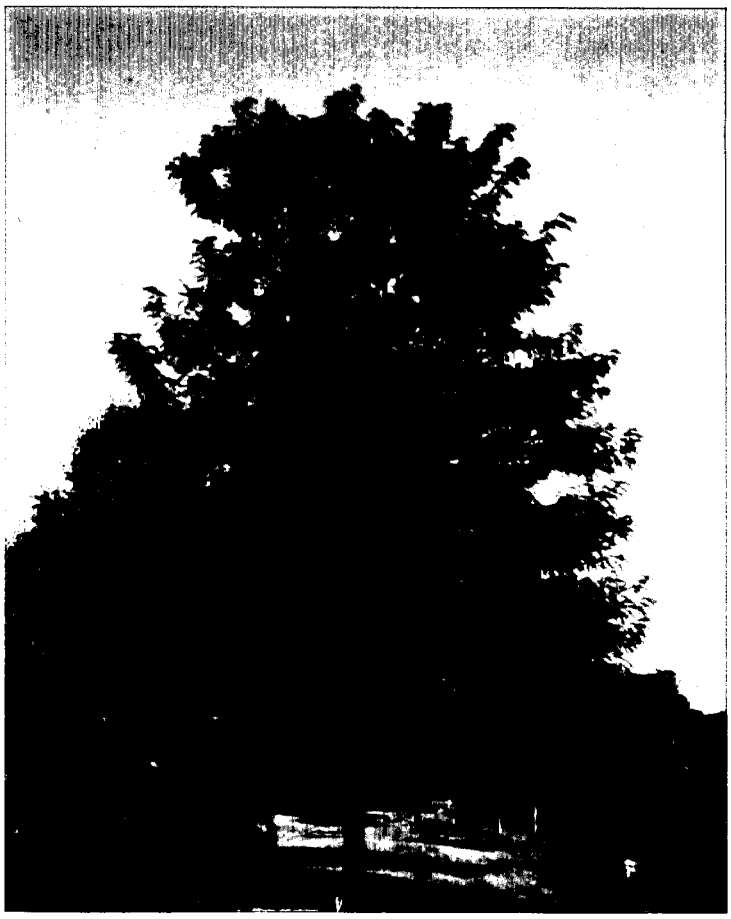
FIG. 1 is a photographic view of the mature tree in leaf showing its distinct broadly pyramidal growth form and heavy dense crown.
Figure 2:
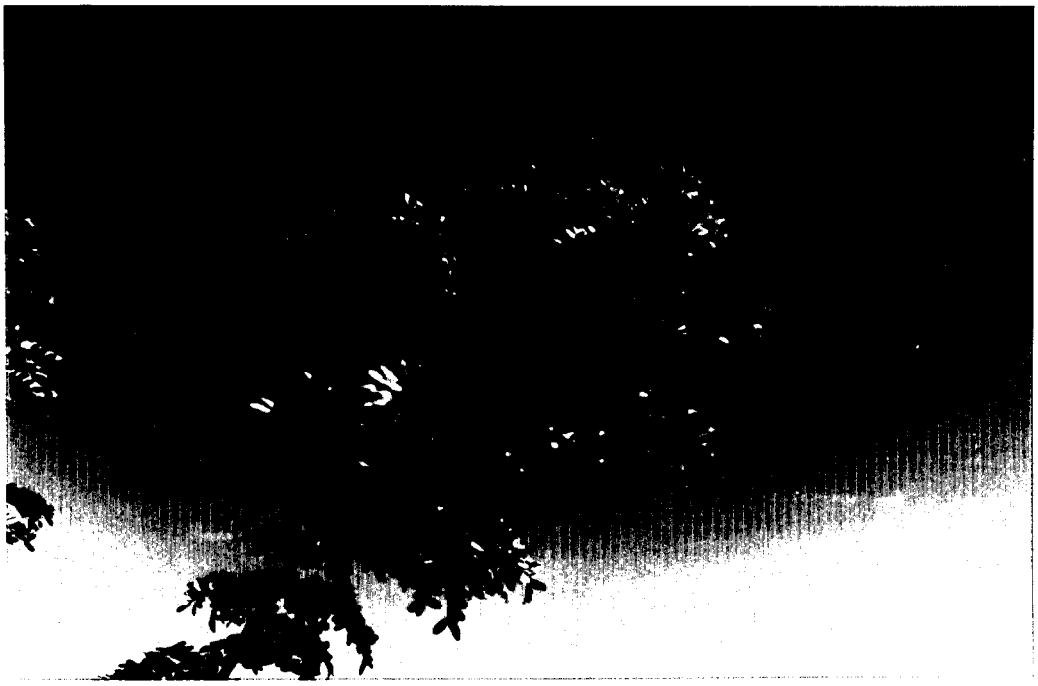
FIG. 2 is a photographic view of the dark green foliage as it appears on the tree.
Figure 3:
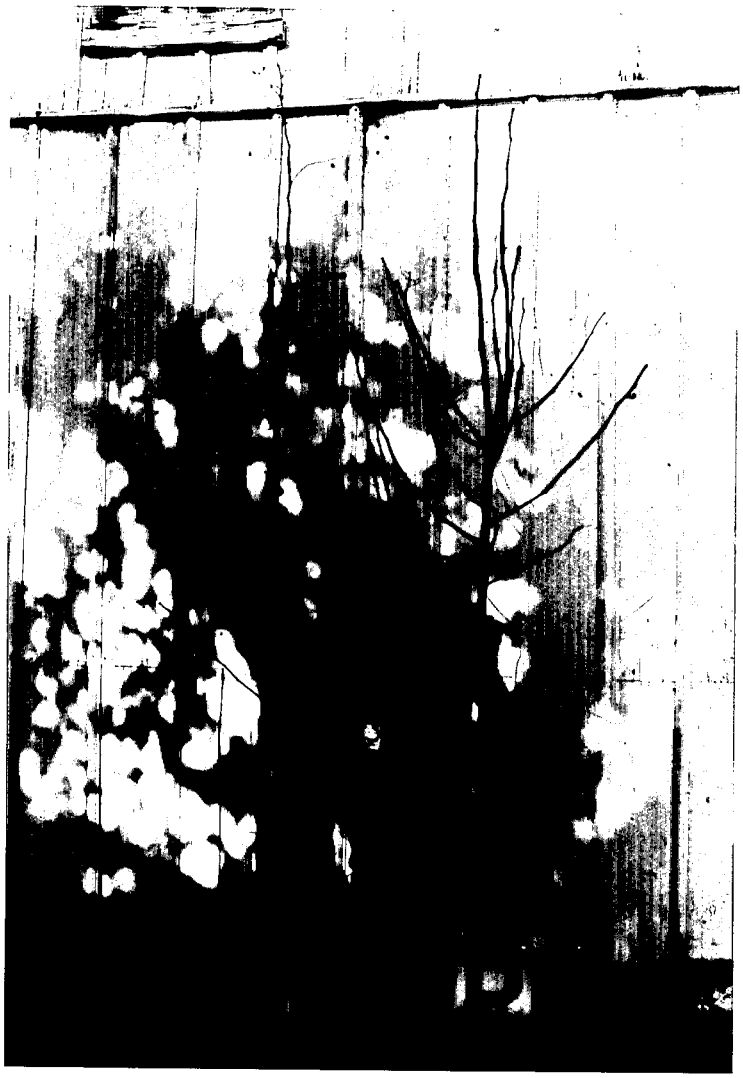
FIG 3 is a photographic view of the caliper and crown development of a two-year-old nursery liner propagated from the parent tree (Tree "B") and demonstrating the more rapid overall development as compared to a typical two-year-old honeylocust cultivar nursery liner (Tree "A").
Figure 4:
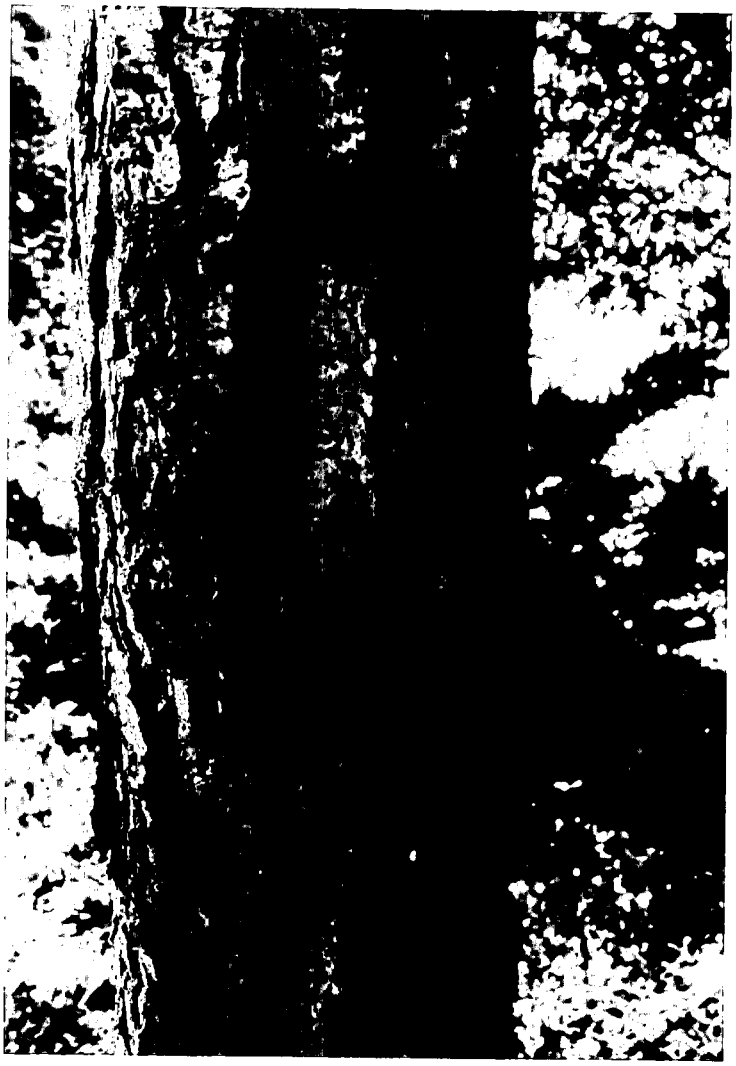
FIG. 4 is a photographic view of the bark on the mature tree.
Figure 5:
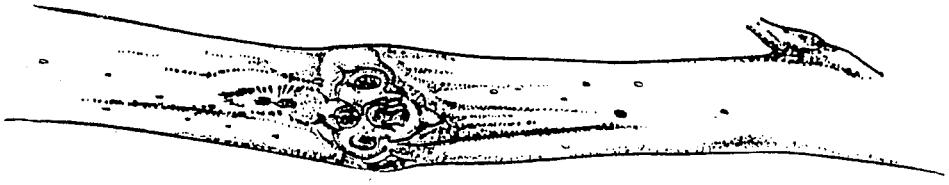
FIG. 5 is a drawing of the leaf scar.

The following is a detailed description of my new variety with color designations according to the R.H.S. Colour Chart published by The Royal Horticultural Society of London, England and the stated observations having been made by the applicant at Madison, Ohio and Oquawka, Ill.

Origin: Seedling.

Parentage: A tree of unknown origin and planted on cultivated property.

Propagation: Maintains its distinguishing characteristics when propagated by budding.

Classification: *Gleditsia triacanthos* var. inermis.

Form: Medium sized tree.

Habit: A medium sized deciduous tree with a single trunk below, soon dividing into several main branches lacking spines, the crown broadly pyramidal, containing many lateral branches.

Growth rate: Rapid.

Bark: Nearly black at maturity, smooth on young trees, becoming divided by deep fissures into long, narrow, longitudinal ridges and roughened on the surface by persistant scales.

Leaves: Alternate, deciduous, evenly once- or twice-pinnately compound, the latter with 7–12 pairs on the pinnae, the leaflets nearly sessile, 10–20 mm long and 4–7 mm wide, ovate or elliptical with blunt apices, rounded bases, and faintly toothed or entire margins, glabrous except for a few hairs on the lower surface and along the margin, bright green above (R.H.S. 135A), paler below, new growth emerging an organ-bronze (R.H.S. 178A), clear yellow in autumn; rachis pubescent, grooved; petiole with swollen base, nearly closing the buds.

Winter buds: Partially covered by the leaf scar, glabrous, dark brown, sessile, superposed; terminal bud lacking.

Twigs: Zig-zagged, reddish brown, marked with small round lenticels, shiny, enlarged at the nodes, lacking spines, with a pinkish pith.

Leaf scars: Alternate, irregularly heart-shaped, with 3 bundle traces, stipule scars absent.

Fruit: None observed, plant believed to be strictly staminate (i.e., male plant.

Flowers: None observed.

I claim:

1. A new variety and the parts thereof, of *Gleditsia triacanthos* var. inermis 'Wandell' as described herein that differs from other varieties by the unique combination of: (1) a distinct broadly pyramidal growth form; (2) a uniform branch angle; (3) a dense compact crown composed of many lateral branches; (4) a high leaf population of deep green foliage; and (5) a rapid rate of growth demonstrated by the development of many lateral branches at an early age and the early development of caliper on juvenile trees propagated from the parent tree.

* * * * *